US008237451B2

(12) United States Patent
Joy et al.

(10) Patent No.: US 8,237,451 B2
(45) Date of Patent: Aug. 7, 2012

(54) COMMUNICATING WITH AN IMPLANTED WIRELESS SENSOR

(75) Inventors: James Joy, Woodstock, GA (US); Jason Kroh, Villa Rica, GA (US); Michael Ellis, Alpharetta, GA (US); Mark Allen, Atlanta, GA (US); Wilton Pyle, Marietta, GA (US)

(73) Assignee: CardioMEMS, Inc., Atlanta, GA (US)

( * ) Notice: Subject to any disclaimer, the term of this patent is extended or adjusted under 35 U.S.C. 154(b) by 0 days.

(21) Appl. No.: 13/078,091

(22) Filed: Apr. 1, 2011

(65) Prior Publication Data

US 2011/0181297 A1 Jul. 28, 2011

Related U.S. Application Data

(60) Division of application No. 12/466,595, filed on May 15, 2009, now Pat. No. 7,932,732, which is a division of application No. 11/613,645, filed on Dec. 20, 2006, now Pat. No. 7,550,978, which is a continuation of application No. 11/105,294, filed on Apr. 13, 2005, now Pat. No. 7,245,117.

(60) Provisional application No. 60/623,959, filed on Nov. 1, 2004.

(51) Int. Cl.
*G01R 27/32* (2006.01)
*G01R 35/00* (2006.01)
*G01R 23/12* (2006.01)

(52) U.S. Cl. .................. 324/633; 324/601; 324/76.53
(58) Field of Classification Search ................. 324/633, 324/601, 76.53
See application file for complete search history.

(56) References Cited

U.S. PATENT DOCUMENTS

| 2,769,553 | A | 6/1957 | Von Wittem |
| 3,867,950 | A | 2/1975 | Fischell |
| 3,882,424 | A | 5/1975 | Debois et al. |
| 3,913,028 | A | 10/1975 | Bosselaers |
| 3,942,382 | A | 3/1976 | Hok |

(Continued)

FOREIGN PATENT DOCUMENTS

AU 701577 B2 2/1999

(Continued)

OTHER PUBLICATIONS

Dehennis, A. et al., "A Passive-Telemetry-Based Pressure Sensing System", Proc. Solid State Sensors and Actuators Workshop, Hilton Head. SC, 2002, pp. 165-168.

(Continued)

*Primary Examiner* — Timothy J Dole
(74) *Attorney, Agent, or Firm* — Kilpatrick Townsend & Stockton LLP

(57) ABSTRACT

The present invention determines the resonant frequency of a sensor by adjusting the phase and frequency of an energizing signal until the frequency of the energizing signal matches the resonant frequency of the sensor. The system energizes the sensor with a low duty cycle, gated burst of RF energy having a predetermined frequency or set of frequencies and a predetermined amplitude. The energizing signal is coupled to the sensor via magnetic coupling and induces a current in the sensor which oscillates at the resonant frequency of the sensor. The system receives the ring down response of the sensor via magnetic coupling and determines the resonant frequency of the sensor, which is used to calculate the measured physical parameter. The system uses a pair of phase locked loops to adjust the phase and the frequency of the energizing signal.

16 Claims, 7 Drawing Sheets

U.S. PATENT DOCUMENTS

| | | | |
|---|---|---|---|
| 3,958,558 A | 5/1976 | Dunphy et al. | |
| 4,026,276 A | 5/1977 | Chubbuck | |
| 4,114,606 A | 9/1978 | Seylar | |
| 4,127,110 A | 11/1978 | Bullara | |
| 4,152,669 A | 5/1979 | Igarashi | |
| 4,206,762 A | 6/1980 | Cosman | |
| 4,207,903 A | 6/1980 | O'Neill | |
| 4,237,900 A | 12/1980 | Schulman et al. | |
| 4,354,506 A | 10/1982 | Sakaguchi et al. | |
| 4,378,809 A | 4/1983 | Cosman | |
| 4,485,813 A | 12/1984 | Anderson et al. | |
| 4,494,950 A | 1/1985 | Fischell | |
| 4,521,684 A | 6/1985 | Gilby et al. | |
| 4,531,526 A | 7/1985 | Genest et al. | |
| 4,593,703 A | 6/1986 | Cosman et al. | |
| 4,596,563 A | 6/1986 | Pande | |
| 4,713,540 A | 12/1987 | Gibly et al. | |
| 4,718,425 A | 1/1988 | Tanaka et al. | |
| 4,720,687 A | 1/1988 | Ostoich et al. | |
| 4,796,641 A | 1/1989 | Mills et al. | |
| 4,815,472 A | 3/1989 | Wise et al. | |
| 4,846,191 A | 7/1989 | Brockway et al. | |
| 4,890,623 A | 1/1990 | Cook et al. | |
| 4,899,752 A | 2/1990 | Cohen | |
| 4,913,147 A | 4/1990 | Fahlstrom et al. | |
| 4,934,369 A | 6/1990 | Maxwell | |
| 4,987,897 A | 1/1991 | Funke | |
| 5,113,868 A | 5/1992 | Wise et al. | |
| 5,115,128 A | 5/1992 | Cook | |
| 5,129,394 A | 7/1992 | Mehra | |
| 5,148,123 A | 9/1992 | Ries | |
| 5,165,289 A | 11/1992 | Tilmans | |
| 5,181,423 A | 1/1993 | Philipps et al. | |
| 5,192,314 A | 3/1993 | Daskalakis | |
| 5,200,930 A * | 4/1993 | Rouquette | 367/76 |
| 5,207,103 A | 5/1993 | Wise et al. | |
| 5,265,606 A | 11/1993 | Kujawski | |
| 5,353,800 A | 10/1994 | Pohndorf et al. | |
| 5,357,253 A * | 10/1994 | Van Etten et al. | 342/22 |
| 5,373,852 A | 12/1994 | Harrison et al. | |
| 5,411,551 A | 5/1995 | Winston et al. | |
| 5,431,171 A | 7/1995 | Harrison et al. | |
| 5,440,300 A | 8/1995 | Spillman, Jr. | |
| 5,487,760 A | 1/1996 | Villafana | |
| 5,497,099 A | 3/1996 | Walton | |
| 5,515,041 A | 5/1996 | Spillman, Jr. | |
| 5,535,752 A | 7/1996 | Halperin et al. | |
| 5,538,005 A | 7/1996 | Harrison et al. | |
| 5,551,427 A | 9/1996 | Altman | |
| 5,566,676 A | 10/1996 | Rosenfeldt et al. | |
| 5,593,430 A | 1/1997 | Renger | |
| 5,594,389 A | 1/1997 | Kiyanagi et al. | |
| 5,600,245 A | 2/1997 | Yamamoto et al. | |
| 5,625,341 A | 4/1997 | Giles et al. | |
| 5,626,630 A | 5/1997 | Markowitz et al. | |
| 5,686,841 A | 11/1997 | Stolarczyk et al. | |
| 5,695,155 A | 12/1997 | Macdonald et al. | |
| 5,702,427 A | 12/1997 | Ecker et al. | |
| 5,703,576 A | 12/1997 | Spillman, Jr. et al. | |
| 5,713,917 A | 2/1998 | Leonhardt et al. | |
| 5,722,414 A | 3/1998 | Archibald et al. | |
| 5,723,791 A | 3/1998 | Koch et al. | |
| 5,743,267 A | 4/1998 | Nikolic et al. | |
| 5,796,827 A | 8/1998 | Coppersmith et al. | |
| 5,807,265 A | 9/1998 | Itoigawa et al. | |
| 5,836,886 A | 11/1998 | Itoigawa et al. | |
| 5,860,938 A | 1/1999 | Lafontaine et al. | |
| 5,896,113 A | 4/1999 | O'Neill | |
| 5,899,927 A | 5/1999 | Ecker et al. | |
| 5,935,084 A | 8/1999 | Southworth | |
| 5,942,991 A | 8/1999 | Gaudreau et al. | |
| 5,967,986 A | 10/1999 | Cimochowski et al. | |
| 5,986,549 A | 11/1999 | Teodorescu | |
| 6,015,386 A | 1/2000 | Kensey et al. | |
| 6,015,387 A | 1/2000 | Schwartz et al. | |
| 6,019,729 A | 2/2000 | Itoigawa et al. | |
| 6,024,704 A | 2/2000 | Meador et al. | |
| 6,025,725 A | 2/2000 | Gershenfeld et al. | |
| 6,030,413 A | 2/2000 | Lazarus | |
| 6,033,366 A | 3/2000 | Brockway et al. | |
| 6,053,873 A | 4/2000 | Govari et al. | |
| 6,076,016 A | 6/2000 | Feierbach | |
| 6,111,520 A | 8/2000 | Allen et al. | |
| 6,113,553 A | 9/2000 | Chubbuck | |
| 6,134,461 A | 10/2000 | Say et al. | |
| 6,140,740 A | 10/2000 | Porat et al. | |
| 6,159,156 A | 12/2000 | Van Bockel | |
| 6,165,135 A | 12/2000 | Neff | |
| 6,198,965 B1 | 3/2001 | Penner et al. | |
| 6,201,980 B1 | 3/2001 | Darrow et al. | |
| 6,203,516 B1 * | 3/2001 | Kepley | 604/22 |
| 6,206,835 B1 | 3/2001 | Spillman, Jr. et al. | |
| 6,237,398 B1 | 5/2001 | Porat et al. | |
| 6,239,724 B1 | 5/2001 | Doron et al. | |
| 6,259,328 B1 | 7/2001 | Wesolowski | |
| 6,277,078 B1 | 8/2001 | Porat et al. | |
| 6,278,379 B1 | 8/2001 | Allen et al. | |
| 6,287,253 B1 | 9/2001 | Ortega et al. | |
| 6,292,104 B1 | 9/2001 | Wakabayashi | |
| 6,327,319 B1 | 12/2001 | Hietala et al. | |
| 6,331,792 B1 | 12/2001 | Tonietto | |
| 6,373,264 B1 | 4/2002 | Matsumoto et al. | |
| 6,409,674 B1 | 6/2002 | Brockway et al. | |
| 6,411,130 B1 | 6/2002 | Gater | |
| 6,442,413 B1 | 8/2002 | Silver | |
| 6,454,720 B1 | 9/2002 | Clerc et al. | |
| 6,466,114 B1 * | 10/2002 | Alexandersson | 334/14 |
| 6,577,893 B1 | 6/2003 | Besson et al. | |
| 6,645,143 B2 | 11/2003 | VanTassel et al. | |
| 6,667,725 B1 | 12/2003 | Simons et al. | |
| 6,743,183 B1 | 6/2004 | Thornton | |
| 6,765,493 B2 | 7/2004 | Londsdale et al. | |
| 6,923,769 B2 | 8/2005 | Nishii et al. | |
| 6,926,670 B2 | 8/2005 | Rich et al. | |
| 6,958,663 B2 * | 10/2005 | Eihama et al. | 333/156 |
| 7,076,215 B1 | 7/2006 | Moliere | |
| 7,233,182 B1 | 6/2007 | Savoj | |
| 7,245,117 B1 | 7/2007 | Joy et al. | |
| 7,265,478 B2 * | 9/2007 | Thiesen | 310/313 R |
| 7,285,958 B2 * | 10/2007 | Overby et al. | 324/326 |
| 7,550,978 B2 | 6/2009 | Joy et al. | |
| 7,699,059 B2 * | 4/2010 | Fonseca et al. | 128/899 |
| 2002/0049394 A1 | 4/2002 | Roy et al. | |
| 2002/0151816 A1 | 10/2002 | Rich et al. | |
| 2002/0188207 A1 | 12/2002 | Richter | |
| 2003/0031587 A1 | 2/2003 | Hu et al. | |
| 2003/0105388 A1 | 6/2003 | Roy et al. | |
| 2003/0136417 A1 | 7/2003 | Fonseca et al. | |
| 2003/0139677 A1 | 7/2003 | Fonseca et al. | |
| 2003/0151400 A1 | 8/2003 | Petrovich et al. | |
| 2003/0185330 A1 | 10/2003 | Hessel et al. | |
| 2004/0122494 A1 | 6/2004 | Eggers et al. | |
| 2004/0181206 A1 | 9/2004 | Chiu et al. | |
| 2004/0211260 A1 | 10/2004 | Girmonsky et al. | |
| 2005/0043670 A1 | 2/2005 | Rosenberg | |
| 2005/0046558 A1 | 3/2005 | Buenz et al. | |
| 2005/0075697 A1 | 4/2005 | Olson et al. | |
| 2005/0085703 A1 | 4/2005 | Behm | |
| 2005/0154321 A1 | 7/2005 | Wolinsky et al. | |
| 2006/0025704 A1 | 2/2006 | Stendel et al. | |
| 2006/0052737 A1 | 3/2006 | Bertrand et al. | |
| 2006/0196277 A1 | 9/2006 | Allen et al. | |
| 2006/0287598 A1 | 12/2006 | Lasater et al. | |
| 2007/0100215 A1 | 5/2007 | Powers et al. | |
| 2007/0210786 A1 | 9/2007 | Allen et al. | |
| 2007/0236213 A1 | 10/2007 | Raden et al. | |
| 2007/0247138 A1 | 10/2007 | Miller et al. | |
| 2008/0077016 A1 | 3/2008 | Sparks et al. | |
| 2009/0224837 A1 | 9/2009 | Ellis et al. | |

FOREIGN PATENT DOCUMENTS

| | | |
|---|---|---|
| CA | 1168061 | 6/1983 |
| DE | 3330519 A1 | 3/1985 |
| DE | 19510452 A1 | 10/1995 |
| DE | 19644858.5 | 10/1996 |
| EP | 0072003 A2 | 2/1983 |
| EP | 0450653 A2 | 10/1991 |

| | | |
|---|---|---|
| EP | 0337035 | 11/1993 |
| EP | 0646365 | 4/1995 |
| JP | 58-70399 A | 4/1983 |
| JP | 63-171331 A | 7/1986 |
| JP | 64-81507 A | 3/1989 |
| JP | 9-259384 A | 10/1997 |
| WO | WO 83/03348 | 10/1983 |
| WO | WO 90/06723 | 6/1990 |
| WO | WO 95/33517 | 12/1995 |
| WO | WO 97/09926 | 3/1997 |
| WO | WO 97/11641 A | 4/1997 |
| WO | WO 97/32518 | 9/1997 |
| WO | WO 97/32519 | 9/1997 |
| WO | WO 97/33513 | 9/1997 |
| WO | WO 99/34731 | 7/1999 |
| WO | WO 00/16686 | 3/2000 |
| WO | WO 01/00089 | 1/2001 |
| WO | WO 01/87137 | 11/2001 |
| WO | WO 01/97908 A2 | 12/2001 |
| WO | WO 03/032009 A | 4/2003 |
| WO | WO 03/061504 A1 | 7/2003 |
| WO | WO 98/47727 A | 10/2003 |
| WO | WO 2005/027998 | 3/2005 |
| WO | WO 2006/049796 A | 5/2006 |

OTHER PUBLICATIONS

Vallabhanena, et al.; "Aortic Side Branch Perfusion Alone Does Not Account for High Intra-Sac Pressure After Endovascular Repair (EVAR) in the Absence of Graft-Related Endoleak", European Journal of Vascular and Endovascular Surgery, vol. 25. Issue 4, pp. 354-359, Mar. 15, 2003.

Gawenda, et al., "Intra-Aneurysm Sac Pressure—The Holy Gail of Endoluminanl Grafting of AAA", Eur J Vasc Endovasc Surg, vol. 24, Aug. 2002, pp. 139-145.

Schurink, et al., "Endoleakage After Stent-Graft Treatment of Abdominal Aneurysm: Implications on Pressure and Imaging—An In Vitro Study": Journal of Vascular Surgery, vol. 28, No. 2, pp. 234-241, Aug. 1998.

Sonesson et al., "Intra-Aneurysm Pressure Measurements in Successfully Excluded Abdominal Aortic Aneurysm After Endovescular Repair": Journal of Vascular Surgery, vol. 37, No. 4, Apr. 2002. pp. 733-736.

Skillern of al., "Endotension in an Experimental Aneurysm Model": Journal of Vascular Surgery. vol. 36, No. 4, Oct. 2002, pp. 814-817.

Treharne et al., "Quality Control During Endovascular Aneurysm Repair: Monitoring Aneurysmal Sac Pressure and Superficial Femoral Artery Flow Velocity": J. Endovasc Surg. 1999, 6, pp. 239-245.

Manwaring et al. "Remote Monitoring of Intercranial Pressure"; Institute of Concology, Annals of the Academy of Studencia Apr. 2001; pp. 77-80.

Schurink et al., "Experiments Study of the Influence of Endoleakage Size on Pressure in the Aneurysm Sac and the Consequences of Thrombosis"; Bristish Journal of Surgery 2002, 87, pp. 71-78.

Ouriel, "Role of Intrasac Pressure Measurements After EVAR: Can They Be Followed Noninvasively?", *Combined Session: Vascular Surgery and Interventional Radiology*, VII 4.1, VEITH Meeting, New York, 2001.

Baum et al , "Aneurysm Sac Pressure measurements After Endovascular Repair of Abdominal Aortic Aneurysms"; Journal of Vascular Surgery, vol. 33. No. 1, Jan. 2001, pp. 32-41.

Harris et al., "Predicting failure of endovascular Aneurysm repair"; Eur J Vas Endovasc Surg. vol. 17, Jan. 1999; pp. 1-2.

Akingba et al., "An Implantable Pressure Sensor for Aneurysmal Disease", Admitted Prior Art.

Adams, JR.; "Guiding Heart Failure Care by Invasive Hemodynamic Measurements: Possible Or Useful?"; Journal of cardiac failure, vol. 8, No. 2. Apr. 2002, pp. 71-73.

Magalski et al., "Continuous Ambulatory Right Heart Presure Measurements with an Implantable Hemodynamic Monitor: A Multicenter, 12-Month Follow-Up Study of Patients With Chronic Heart Failure"; Journal of Cardiac failure, vol. 8. Apr. 2002. pp. 63-70.

Shabetai, "Monitoring Heart Failure Hemodynamics with an Implanted Device: Its Potential to Improve Outcome"; Journal of the American College of Cardiology: vol. 41, No. 4. Feb. 19, 2003. pp. 572-573.

Parodi et al., "Intra-eneurysmal Pressure After Incomplete Endovascular Exclusion"; Journal of Vascular Surgery, vol. 24, No. 5, Nov. 2001, pp. 909-914.

Gawenda et al., "Pressure is Transmitted Through PTFE and Dacron Grafts Leading the Aneurysm Sac Pressure Endoluminal Grafting of AAA—An In Vitro Study"; Vascular Centre, University of Cologne, Germany.

Akin et al., "RF Telemetry Powering and Controlling of Hermetically Sealed Integrated Sensors and Actuators"; Center for Integrated Sensors and Circuits; Department of Electrical Engineering and Computer Science; University of Michigan; Ann Arbor, Michigan 48109-2122; pp. 145-148, 1990.

Haynes, et al., "Medical Electronics: The Pill That Talks", *DEP. Camden N.J.*, RCE Engineer, vol. 5, Feb.-Mar. 1960.

Dehennis, A. et al., "A Double-Sided Single-Chip Wireless Pressure Sensor", Dig. IEEE MEMS Conf., Jan. 2002, pp. 252-255.

Zhe et al., "A MEMS Device for Measurerment of Skin Friction With Capacitive Sensing", Proc. of IEEE MEMS, 2001.

Chuter et al., "Endovascular and Surgical techniques"; Eur J. Vasc Endovasc Surg vol. 13, Jan. 1997, pp. 85-87.

Farrar et al., "Telemetering of Intraenteric pressure in man by an Externally Energized Wireless Capsule"; Science, New Series, vol. 131, Issue 3416 (Jun. 17, 1960), 1814.

Allen, "Micromachined Endovascularly Implantable Wireless Aneurysm Pressure Sensors", International Conference on Solid State Sensors. Actuators and Microsystems, No. 13, 2005, pp. 275-278.

Fonseca, "High Temperature Characterization of Ceramic Pressure Sensors", vol. 1, 2001 , pp. 486-489.

Harpster, "A Passive Wireless Integrated Humidity Sensor", Micro Etectro Mechanical Systems, 2001, Vol. IEEEMEMSCONF, No. 14, pp. 553-557.

Seifert, et al., "Wirelessly Interrogable Acoustic Sensors", Frequency and Time Form, (ONLINE) No. 4, 1999 , pp. 1013-1018.

International Search Report, PCT International Patent Application No. PCT/US2010/033396, mailed Jan. 7, 2011.

International Search Report, PCT International Patent Application No. PCT/US2009/039220, mailed Nov. 17, 2009.

Supplementary European Search Report, European Patent Application No. 05805691.2, mailed Feb. 1 , 2012.

* cited by examiner

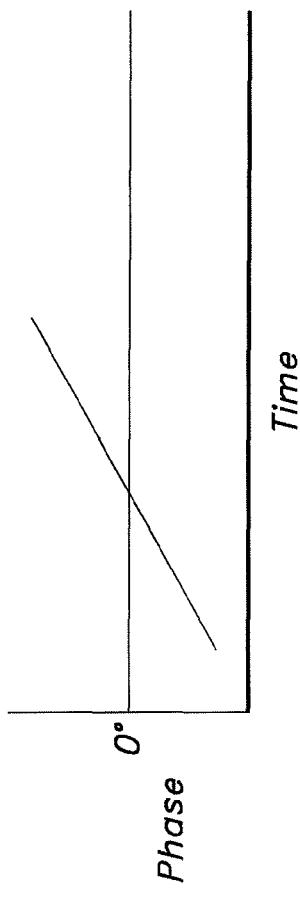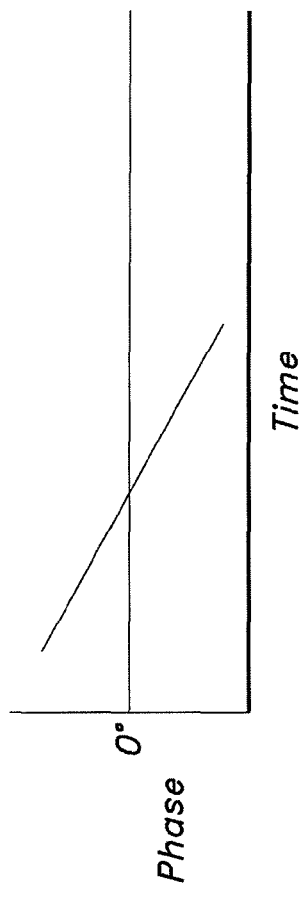

COMMUNICATING WITH AN IMPLANTED WIRELESS SENSOR

RELATED APPLICATIONS

This application is a divisional patent application of U.S. patent application Ser. No. 12/466,595, now U.S. Pat. No. 7,932,732, entitled "Preventing a False Lock in a Phase Lock Loop" filed May 15, 2009, which is a divisional patent application of U.S. patent application Ser. No. 11/613,645, now U.S. Pat. No. 7,550,978, entitled "Communication with an Implanted Wireless Sensor" filed Dec. 20, 2006 which is a continuation patent application of U.S. patent application Ser. No. 11/105,294, now U.S. Pat. No. 7,245,117 entitled "Communication with an Implanted Wireless Sensor" filed Apr. 13, 2005, which claims priority to U.S. Provisional Application No. 60/623,959 entitled "Communicating with an Implanted Wireless Sensor" filed Nov. 1, 2004, all of which are incorporated herein by reference. This application is also related to U.S. patent application Ser. No. 12/466,541, now U.S. Pat. No. 7,839,153, entitled "Communicating with an Implanted Wireless Sensor" filed on May 15, 2009, which is incorporated herein by reference.

TECHNICAL HELD

The present invention is directed in general to communicating with a wireless sensor, and in particular to communicating with a wireless sensor implanted within the body to measure a physical condition.

BACKGROUND

Wireless sensors can be implanted within the body and used to monitor physical conditions, such as pressure or temperature. For example, U.S. Pat. No. 6,111,520, U.S. Pat. No. 6,855,115 and U.S. Pat. No. 7,699,059, each of which is incorporated herein by reference, all describe wireless sensors that can be implanted within the body. These sensors can be used to monitor physical conditions within the heart or an abdominal aneurysm. An abdominal aortic aneurysm (AAA) is a dilatation and weakening of the abdominal aorta that can lead to aortic rupture and sudden death. In the case of a repaired abdominal aneurysm, a sensor can be used to monitor pressure within the aneurysm sac to determine whether the intervention is leaking. The standard treatment for AAAs employs the use of stent-grafts that are implanted via endovascular techniques. However, a significant problem that has emerged with these stein-grafts for AAAs is acute and late leaks of blood into the aneurysms sac. Currently, following stent-graft implantation, patients are subjected to periodic evaluation via abdominal CT (Computed Tomography) with IV contrast to identify the potential presence of stent-graft leaks. This is an expensive, risky procedure that lacks appropriate sensitivity to detect small leaks.

Typically, the sensors utilize an inductive-capacitive ("LC") resonant circuit with a variable capacitor. The capacitance of the circuit varies with the pressure of the environment, in which the sensor is located and thus, the resonant frequency of the circuit varies as the pressure varies. Thus, the resonant frequency of the circuit can be used to calculate pressure.

Ideally, the resonant frequency is determined using a non-invasive procedure. Several examples of procedures for determining the resonant frequency of an implanted sensor are discussed in U.S. Pat. No. 6,111,520. Some of the procedures described in the patent require the transmission of a signal having multiple frequencies. A drawback of using a transmission signal having multiple frequencies is that the energy in the frequency bands outside the resonant frequency is wasted. This excess energy requires more power which results in an increase in cost, size, and thermal requirements, as well as an increase in electromagnetic interference with other signals. Thus, there is a need for an optimized method that is more energy efficient and requires less power.

There are unique requirements for communicating with an implanted sensor. For example, the system must operate in a low power environment and must be capable of handling a signal from the sensor with certain characteristics. For example, the signal from the sensor is relatively weak and must be detected quickly because the signal dissipates quickly. These requirements also impact the way that common problems are handled by the system. For example, the problems of switching transients and false locking need to be handled in a manner that accommodates the sensor signal characteristics. Thus, there is a need for a method for communicating with a wireless sensor that operates in a low power environment and that efficiently determines the resonant frequency of the sensor.

The resonant frequency of the sensor is a measured parameter that is correlated with the physical parameter of interest. To be clinically useful there must be means to ensure that variations in measurement environment do not affect the accuracy of the sensor. Thus, there is a need for a system and method for communicating with a wireless sensor that considers variations in the measurement environment.

SUMMARY OF THE INVENTION

The primary goal of aneurysm treatment is to depressurize the sac and to prevent rupture. Endoleaks, whether occurring intraoperatively or postoperatively, can allow the aneurysmal sac to remain pressurized and therefore, increase the chance of aneurysm rupture. The current imaging modalities angiography and CT scan are not always sensitive enough to detect endoleaks or stent graft failure. Intrasac pressure measurements provide a direct assessment of sac exclusion from circulation and may therefore offer intraoperative and post operative surveillance advantages that indirect imaging studies do not.

In one application of the present invention, an AAA pressure sensor is placed into the aneurysm sac at the time of stent-graft insertion. The pressure readings are read out by the physician by holding an electronic instrument, which allows an immediate assessment of the success of the stent-graft at time of the procedure and outpatient follow-up visits, by reading the resonant frequency of the wireless sensor and correlating the frequency reading to pressure.

The present invention meets the needs described above by providing a system and method for communicating with a wireless sensor to determine the resonant frequency of the sensor. The system energizes the sensor with a low duty cycle, gated burst of RF energy having a predetermined frequency or set of frequencies and a predetermined amplitude. The energizing signal is coupled to the sensor via a magnetic loop. The sensor may be an inductive-capacitive ("LC") resonant circuit with a variable capacitor that is implanted within the body and used to measure physical parameters, such as pressure or temperature. The energizing signal induces a current in the sensor which is maximized when the energizing frequency is the same as the resonant frequency of the sensor. The system receives the ring down response of the sensor via magnetic coupling and determines the resonant frequency of the sensor, which is used to calculate the measured physical parameter.

In one aspect of the invention a pair of phase locked loops ("PLLs") is used to adjust the phase and the frequency of the energizing signal until its frequency locks to the resonant frequency of the sensor. In one embodiment, one PLL samples during the calibration cycle and the other PLL samples during the measurement cycle. These cycles alternate every 10 microseconds synchronized with the pulse repetition period. The calibration cycle adjusts the phase of the energizing signal to a fixed reference phase to compensate for system delay or varying environmental conditions. The environmental conditions that can affect the accuracy of the sensor reading include, but are not limited to proximity of reflecting or magnetically absorptive objects, variation of reflecting objects located within transmission distance, variation of temperature or humidity which can change parameters of internal components, and aging of internal components.

One of the PLLs is used to adjust the phase of the energizing signal and is referred to herein as the fast PLL. The other PLL is used to adjust the frequency of the energizing signal and is referred to herein as the slow PLL. During the time that the energizing signal is active, a portion of the signal enters the receiver and is referred to herein as a calibration signal. The calibration signal is processed and sampled to determine the phase difference between its phase and the phase of a local oscillator (referred to herein as the local oscillator 2). The cycle in which the calibration signal is sampled is referred to as the calibration cycle. The system adjusts the phase of the energizing signal to drive the phase difference to zero or another reference phase.

During the measurement cycle, the signal coupled from the sensor (referred to herein as the coupled signal or the sensor signal) is processed and sampled to determine the phase difference between the coupled signal and the energizing signal. The system then adjusts the frequency of the energizing signal to drive the phase difference to zero or other reference phase. Once the slow PLL is locked, the frequency of the energizing signal is deemed to match the resonant frequency of the sensor. The operation of the slow PLL is qualified based on signal strength so that the slow PLL does not lock unless the strength of the coupled signal meets a predetermined signal strength threshold.

The system also handles false locking and switching transients. A false lock occurs if the system locks on a frequency that does not correspond to the resonant frequency of the sensor. In one aspect of the invention, the system avoids false locks by examining how the phase difference signal goes to zero. If the slope of the phase difference signal relative to time meets a predetermined direction, e.g. positive, then the PLL is allowed to lock. However, if the slope of the phase difference signal relative to time does not meet the predetermined direction, e.g. it is negative, then the signal strength is suppressed to prevent a false lock.

Another aspect of the invention uses frequency dithering to avoid a false lock. A constant pulse repetition frequency can add spectral components to the sensor signal and cause a false lock. By randomly varying the pulse repetition frequency of the energizing signal, the sidebands move back and forth so that the average of the sidebands is reduced. Thus, the system locks on the center frequency rather than the sidebands.

In another aspect of the invention, phase dithering can be used to reduce switching transients. The phase of the energizing signal and a local oscillator (referred to herein as local oscillator 1) are randomly changed. Varying the phase of the energizing signal varies the phase of the coupled signal, but does not affect the phase of the transient signal. Thus, the average of the transient signal is reduced. Changing the resonant frequency of the coil as it is switched from energizing mode to coupling mode also reduces switching transients. The capacitors that are connected to the coil are switched between different modes to slightly change the resonant frequency in order to reduce switching transients.

These and other aspects, features and advantages of the present invention may be more clearly understood and appreciated from a review of the following detailed description of the disclosed embodiments and by reference to the appended drawings and claims.

BRIEF DESCRIPTION OF THE DRAWINGS

FIGS. 4(a) and 4(b) are graphs illustrating exemplary phase difference signals in accordance with an embodiment of the invention.

DETAILED DESCRIPTION

The present invention is directed towards a system and method for communicating with a wireless sensor. Briefly described, the present invention determines the resonant frequency of the sensor by adjusting the phase and frequency of an energizing signal until the frequency of this signal locks to the resonant frequency of the sensor. The system energizes the sensor with a low duty cycle, gated burst of RF energy of a predetermined frequency or set of frequencies and predetermined amplitude. This signal induces a current in the sensor that can be used to track the resonant frequency of the sensor. The system receives the ring down response of the sensor and determines the resonant frequency of the sensor, which is used to calculate the measured physical parameter. The system uses a pair of phase locked loops ("PLL"s) to adjust the phase and the frequency of the energizing signal to track the resonant frequency of the sensor.

Exemplary System

Figure 1:
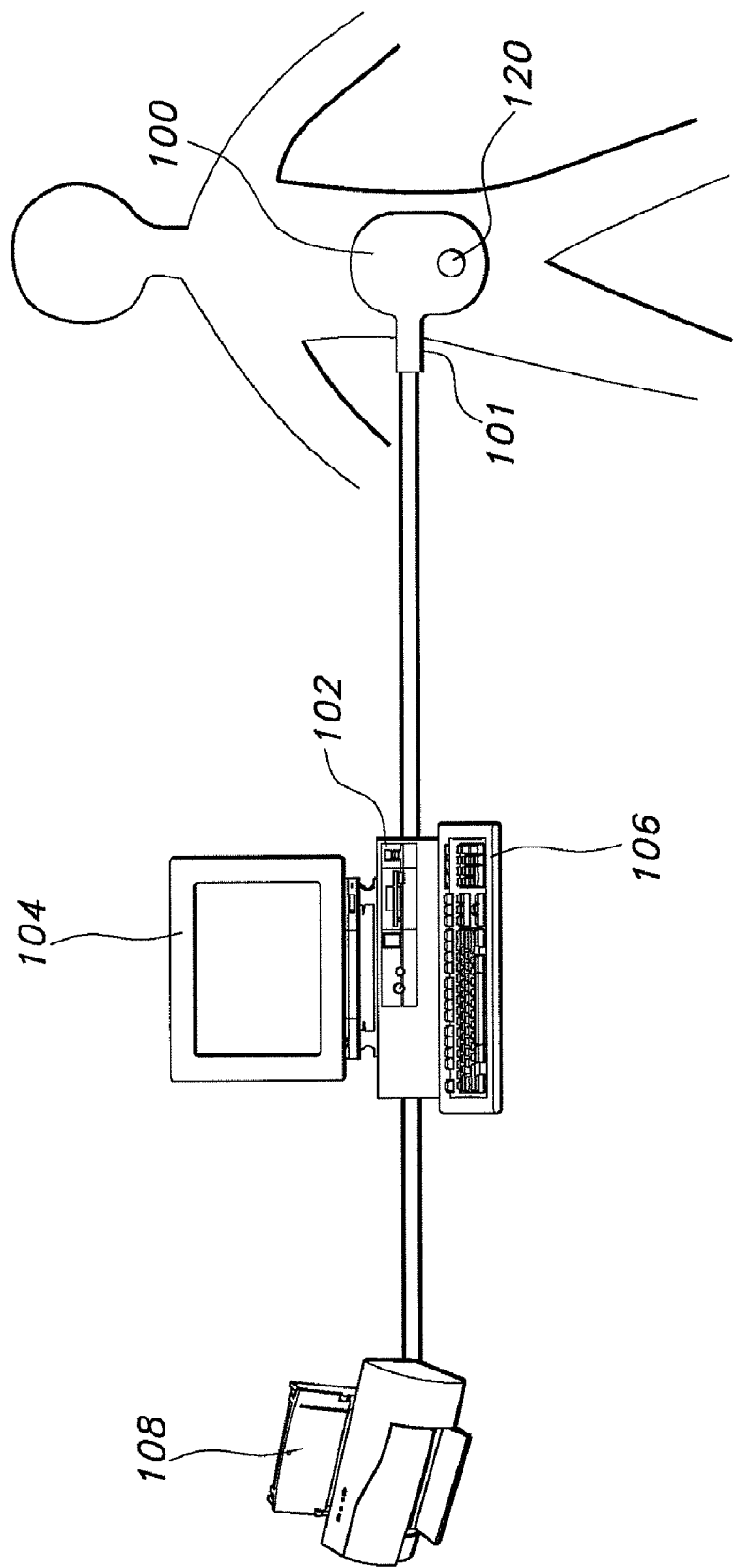
FIG. 1 is a block diagram of an exemplary system for communicating with a wireless sensor in accordance with an embodiment of the invention.

FIG. 1 illustrates an exemplary system for communicating with a wireless sensor implanted within a body. The system includes a coupling loop 100, a base unit 102, a display device 104 and an input device 106, such as a keyboard.

The coupling loop is formed from a band of copper. In one embodiment, the loop is eight inches in diameter. The coupling loop includes switching and filtering circuitry that is enclosed within a shielded box 101. The loop charges the sensor and then couples signals from the sensor into the receiver. The antenna can be shielded to attenuate in-band noise and electromagnetic emissions.

Figure 7:
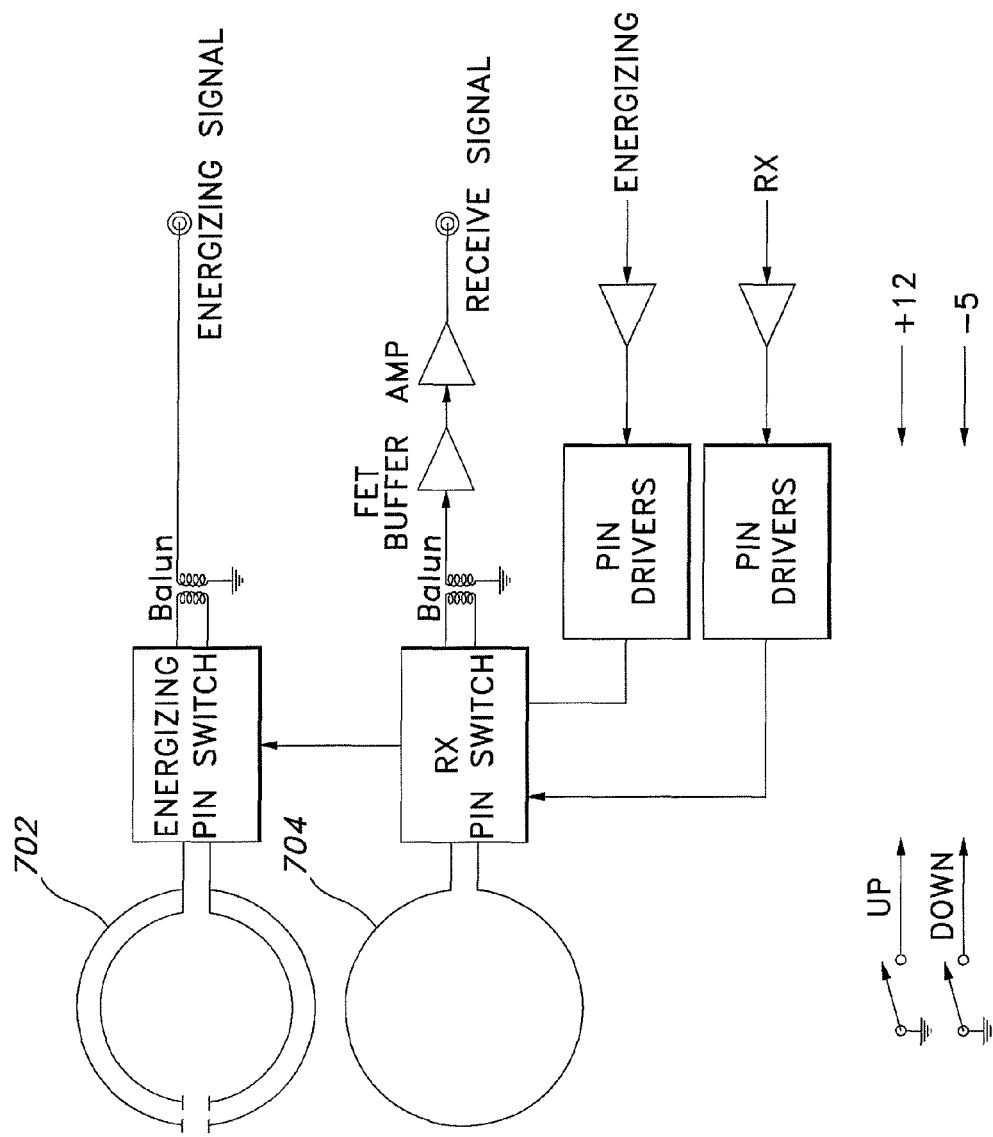
FIG. 7 illustrates a coupling loop in accordance with an embodiment of the invention.

Another possible embodiment for a coupling loop is shown in FIG. 7, which shows separate loops for energizing 702 and for receiving 704, although a single loop can be used for both functions. PIN diode switching inside the loop assembly is used to provide isolation between the energizing phase and the receive phase by opening the RX path pin diodes during the energizing period, and opening the energizing path pin diodes during the coupling period. Multiple energizing, loops can be staggered tuned to achieve a wider bandwidth of matching between the transmit coils and the transmit circuitry.

The base unit includes an RF amplifier, a receiver, and signal processing circuitry. Additional details of the circuitry are described below in connection with FIG. 3.

The display 104 and the input, device 106 are used in connection with the user interface for the system. In the embodiment illustrated in FIG. 1 the display device and the input device are connected to the base unit. In this embodiment, the base unit also provides conventional computing, functions. In other embodiments, the base unit can be connected to a conventional computer, such as a laptop, via a communications link, such as an RS-232 link. If a separate computer is used, then the display device and the input devices associated with the computer can be used to provide the user interface, in one embodiment, LABVIEW software is used to provide the user interface, as well as to provide graphics, store and organize data and perform calculations for calibration and normalization. The user interface records and displays patient data and guides the user through surgical and follow-up procedures.

An optional printer 108 is connected to the base unit and can be used to print out patient data or other types of information. As will be apparent to those skilled in the art other configurations of the system, as well as additional or fewer components can be utilized with the invention.

Patient and system information can be stored within a removable data storage unit, such as a portable USB storage device, floppy disk, smart card, or any other similar device. The patient information can be transferred to the physician's personal computer for analysis, review, or storage. An optional network connection can be provided to automate storage or data transfer. Once the data is retrieved from the system, a custom or third party source can be employed to assist the physician with data analysis or storage.

FIG. 1 illustrates the system communicating with a sensor 120 implanted in a patient. The system is used in two environments: 1) the operating room during implant and 2) the doctor's office during follow-up examinations. During implant the system is used to record at least two measurements. The first measurement is taken during introduction of the sensor for calibration and the second measurement is taken after placement for functional verification. The measurements can be taken by placing the coupling loop either on or adjacent to the patient's hack or the patient's stomach for a sensor that measures properties associated with an abdominal, aneurysm. For other types of measurements, the coupling loop may be placed in other locations. For example, to measure properties associated with the heart, the coupling loop can be placed on the patient's back or the patient's chest.

The system communicates with the implanted sensor to determine the resonant frequency of the sensor. As described in more detail in the patent documents referenced in the Background section, a sensor typically includes an inductive-capacitive ("LC") resonant circuit having a variable capacitor. The distance between the plates of the variable capacitor varies as the surrounding pressure varies. Thus, the resonant frequency of the circuit can be used to determine the pressure.

Figures 2A, 2B, 2C, 2D:
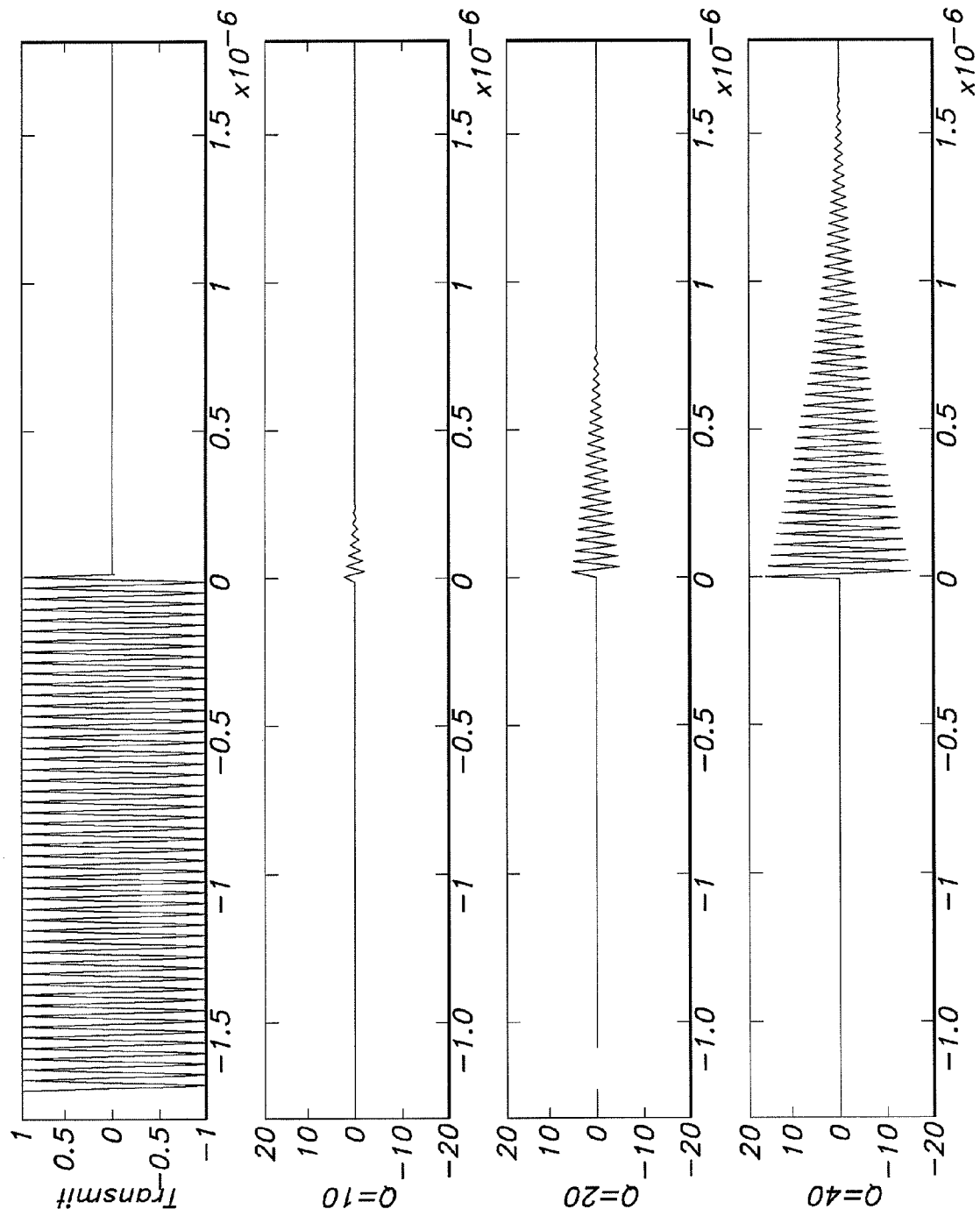
FIG. 2(a) is a graph illustrating an exemplary energizing signal in accordance with an embodiment of the invention.
FIGS. 2(b), 2(c) and 2(d) are graphs illustrating exemplary coupled signals in accordance with an embodiment of the invention.
Figure 8:
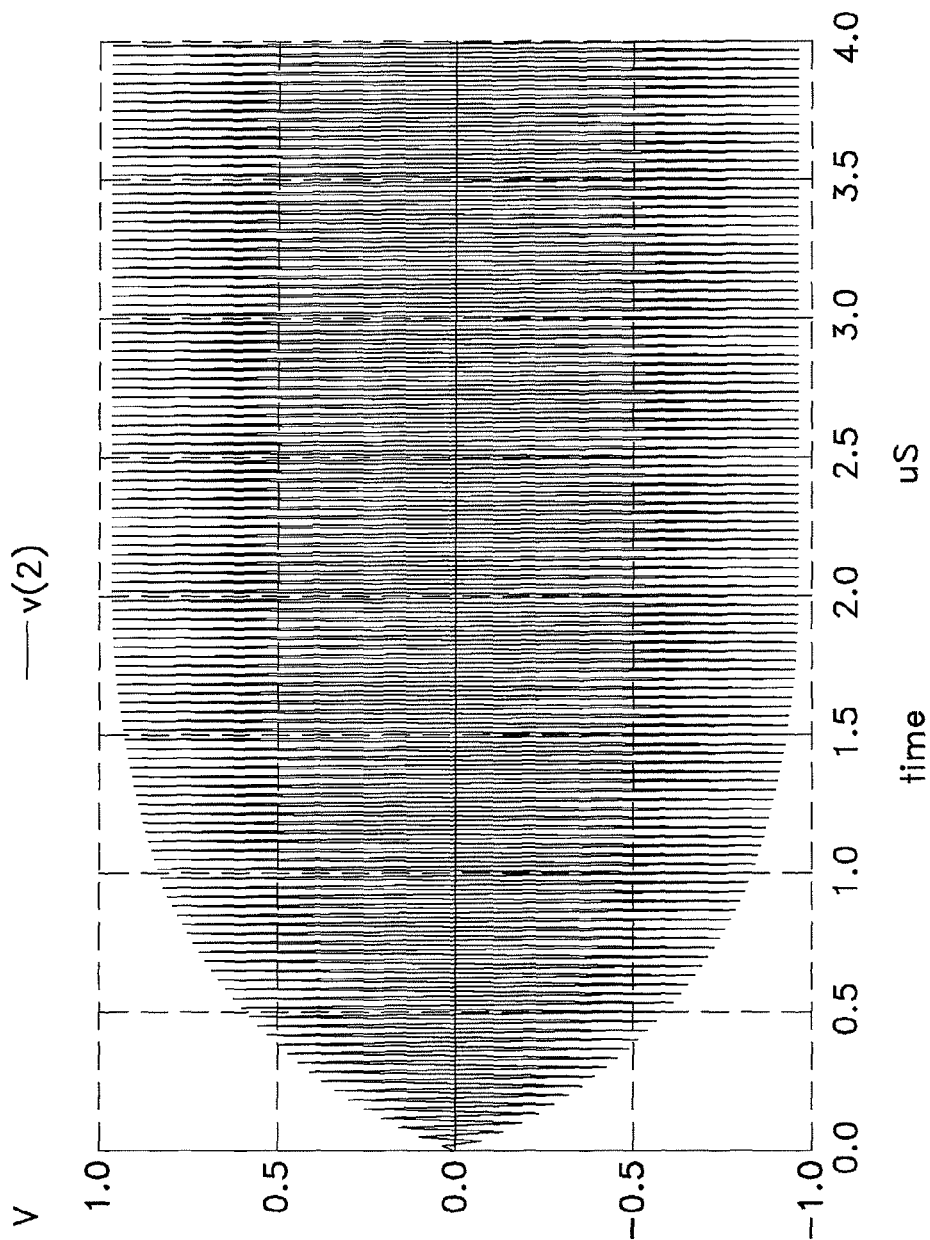
FIG. 8 is a graph illustrating an exemplary charging response of an LC circuit in accordance with an embodiment of the invention.

The system energizes the sensor with an RF burst. The energizing signal is a low duty cycle, gated burst of RF energy of a predetermined frequency or set of frequencies and a predetermined amplitude. Typically, the duty cycle of the energizing signal ranges from 0.1% to 50%. In one embodiment, the system energizes the sensor with a 30-37 MHz fundamental signal at a pulse repetition rate of 100 kHz with a duty cycle of 20%. The energizing signal is coupled to the sensor via a magnetic loop. This signal induces a current in the sensor which has maximum amplitude at the resonant frequency of the sensor. During this time, the sensor charges exponentially to a steady-state amplitude that is proportional to the coupling efficiency, distance between the sensor and loop, and the RF power. FIG. 8 shows the charging response of a typical LC circuit to a burst of RF energy at its resonant frequency. The speed at which the sensor charges is directly related to the Q (quality factor) of the sensor. Therefore, the "on time" of the pulse repetition duty cycle is optimized for the Q of the sensor. The system receives the ring down response of the sensor via magnetic coupling and determines the resonant frequency of the sensor. FIG. 2(a) illustrates a typical energizing signal and FIGS. 2(b), 2(c) and 2(d) illustrate typical coupled signals for various values of Q (quality factor) for the sensor. When the main unit is coupling energy at or near the resonant frequency of the sensor, the amplitude of the sensor return is maximized, and the phase of the sensor return will be close to zero degrees with respect to the energizing phase. The sensor return signal is processed via phase-locked-loops to steer the frequency and phase of the next energizing pulse.

Operation of the Base Unit

Figure 3:
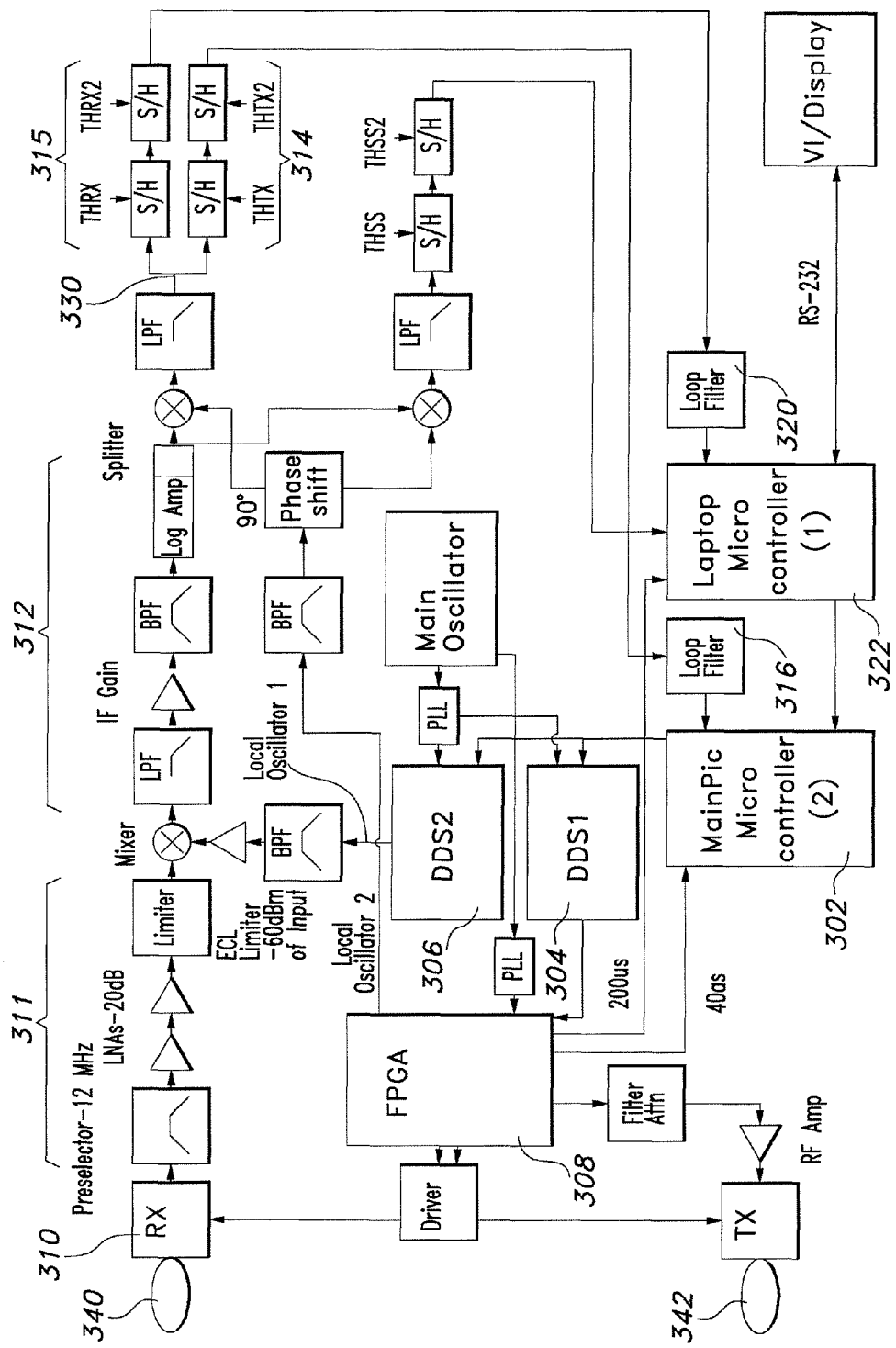
FIG. 3 is a block diagram of an exemplary base unit in accordance with an embodiment of the invention.

FIG. 3 is a block diagram of the signal processing components within an exemplary base unit. The base unit determines the resonant frequency of the sensor by adjusting the energizing signal so that the frequency of the energizing signal matches the resonant frequency of the sensor. In the embodiment illustrated by FIG. 3, two separate processors 302, 322 and two separate coupling loops 340, 342 are shown. In one embodiment, processor 302 is associated with the base unit and processor 322 is associated with a computer connected to the base unit. In other embodiments, a single processor is used that provides the same functions as the two separate processors. In other embodiments a single loop is used for both energizing and for coupling the sensor energy back to the receiver. As will be apparent to those skilled in the art, other configurations of the base unit are possible that use different components.

The embodiment illustrated by FIG. 3 includes a pair of phase lock loops ("PLL"). One of the PLLs is used to adjust the phase of the energizing signal and is referred to herein as the fast PLL. The other PLL is used to adjust the frequency of the energizing signal and is referred to herein as the slow PLL. The base unit provides two cycles: the calibration cycle and the measurement cycle. In one embodiment, the first cycle is a 10 microsecond energizing period for calibration of the system, which is referred to herein as the calibration cycle, and the second cycle is a 10 microsecond energizing/coupling period for energizing the sensor and coupling a return signal from the sensor, which is referred to herein as the measurement cycle. During the calibration cycle, the system generates a calibration signal for system and environmental phase calibration and during the measurement cycle the system both sends and listens for a return signal, i.e. the sensor ring down. Alternatively, as those skilled in the art will appreciate, the calibration cycle and the measurement cycle can be implemented in the same pulse repetition period.

The phase of the energizing signal is adjusted during the calibration cycle by the fast PLL and the frequency of the energizing signal is adjusted during the measurement cycle by the slow PLL. The following description of the operation of the PLLs is presented sequentially for simplicity. However, as those skilled in the art will appreciate, the PLLs actually operate simultaneously.

Initially the frequency of the energizing signal is set to a default value determined by the calibration parameters of the sensor. Each sensor is associated with a number of calibration parameters, such as frequency, offset, and slope. An operator of the system enters the sensor calibration parameters into the system via the user interface and the system determines an initial frequency for the energizing signal based on the particular sensor. Alternatively, the sensor calibration information could be stored on portable storage devices, bar codes, or incorporated within a signal returned from the sensor. The initial phase of the energizing signal is arbitrary.

The initial frequency and the initial phase are communicated from the processor 302 to the DDSs (direct digital synthesizers) 304, 306. The output of DDS1 304 is set to the initial frequency and initial phase and the Output of DDS2 306 (also referred to as local oscillator 1) is set to the initial frequency plus the frequency of the local oscillator 2. The phase of DDS2 is a fixed constant. In one embodiment, the frequency of local oscillator 2 is 4.725 MHz. The output of DDS1 is gated by the field programmable gate array (FPGA) 308 to create a pulsed transmit signal having a pulse repetition frequency ("PRF"). The FPGA provides precise gating so that the base unit can sample the receive signal during specific intervals relative to the beginning or end of the calibration cycle.

During the calibration cycle, the calibration signal which enters the receiver 310 is processed through the receive section 311 and the IF section 312, and is sampled. In one embodiment, the calibration signal is the portion of the energizing signal that leaks into the receiver (referred to herein as the energizing leakage signal). The signal is sampled during the on time of the energizing signal by a sample and hold circuit 314 to determine the phase difference between the signal and local oscillator 2. In the embodiment where the calibration signal is the portion of the energizing signal that leaks into the receiver, the signal is sampled approximately 100 ns after the beginning of the energizing signal pulse. Since the energizing signal is several orders of magnitude greater than the coupled signal, it is assumed that the phase information associated with the leaked signal is due to the energizing signal and the phase delay is due to the circuit elements in the coupling loop, circuit elements in the receiver, and environmental conditions, such as proximity of reflecting objects.

The phase difference is sent to a loop filter 316. The loop filter is set for the dynamic response of the first PLL. In one embodiment, the PLL bandwidth is 1000 Hz and the damping ratio is 0.7. A DC offset is added to allow for positive and negative changes. The processor 302 reads its analog to digital converter (A/D) port to receive the phase difference information and adjusts the phase sent to direct digital synthesizer 1 (DDS1) to drive the phase difference to zero. This process is repeated alternatively until the phase difference is zero or another reference phase.

The phase adjustment made during the energizing period acts to zero the phase of the energizing signal with respect to local oscillator 2. Changes in the environment of the antenna or the receive chain impedance, as well as the phase delay within the circuitry prior to sampling affect the phase difference reading and are accommodated by the phase adjustment.

During the measurement cycle, the energizing signal may be blocked from the receiver during the on time of the energizing signal. During the off time of the energizing signal, the receiver is unblocked and the coupled signal from the sensor (referred to herein as the coupled signal or the sensor signal) is received. The coupled signal is amplified and filtered through the receive section 311. The signal is down converted and additional amplification and filtering takes place in the IF section 312. In one embodiment, the signal is down converted to 4.725 MHz. After being processed through the IF section, the signal is mixed with local oscillator 2 and sampled by sample and hold circuits 315 to determine the phase difference between the coupled signal and the energizing signal. In one embodiment, the sampling occurs approximately 30 ns after the energizing signal is turned off.

In other embodiments, group delay or signal amplitude is used to determine the resonant frequency of the sensor. The phase curve of a second order system passes through zero at the resonant frequency. Since the group delay i.e. derivative of the phase curve reaches a maximum at the resonant frequency, the group delay can be used to determine the resonant frequency. Alternatively, the amplitude of the sensor signal can be used to determine the resonant frequency. The sensor acts like a bandpass filter so that the sensor signal reaches a maximum at the resonant frequency.

The sampled signal is accumulated within a loop filter 320. The loop filter is set for the dynamic response of the slow PLL to aid in the acquisition of a lock by the slow PLL. The PLLs are implemented with op-amp low pass filters that feed A/D inputs on microcontrollers, 302 and 322, which in turn talk to the DDSs, 304 and 306, which provide the energizing signal and local oscillator 1. The microcontroller that controls the energizing DDS 304 also handles communication with the display. The response of the slow PLL depends upon whether the loop is locked or not. If the loop is unlocked, then the bandwidth is increased so that the loop will lock quickly. In one embodiment, the slow PLL has a damping ratio of 0.7 and a bandwidth of 120 Hz when locked (the Nyquist frequency of the blood pressure waveform), which is approximately ten times slower than the fast PLL.

A DC offset is also added to the signal to allow both a positive and a negative swing. The output of the loop filter is input to an A/D input of processor 322. The processor determines a new frequency and sends the new frequency to the DSSs. The processor offsets the current frequency value of the energizing signal by an amount that is proportional to the amount needed to drive the output of the slow PLL loop filter to a preset value. In one embodiment the preset value is 2.5V and zero in phase. The proportional amount is determined by the PLL's overall transfer function.

The frequency of the energizing signal is deemed to match the resonant frequency of the sensor when the slow PLL is locked. Once the resonant frequency is determined, the physical parameter, such, as pressure, is calculated using the calibration parameters associated with the sensor, which results in a difference frequency that is proportional to the measured pressure.

The operation of the slow PLL is qualified based on signal strength. The base unit includes signal strength detection circuitry. If the received signal does not meet a predetermined signal strength threshold, then the slow PLL is not allowed to lock and the bandwidth and search window for the PLL are expanded. Once the received signal meets the predetermined signal strength threshold, then the bandwidth and search window of the slow PLL is narrowed and the PLL can lock. In the preferred embodiment, phase detection, and signal strength determination are provided via the "I" (in phase) and "Q" (quadrature) channels of a quadrature mixer circuit. The "I" channel is lowpass filtered and sampled to provide signal strength information to the processing circuitry. The "Q" channel is lowpass filtered and sampled to provide phase error information to the slow PLL.

Avoiding False Locks

The system provides unique solutions to the false lock problem. A false lock occurs if the system locks on a frequency that does not correspond to the resonant frequency of the sensor. There are several types of false locks. The first type of false lock arises due to the pulsed nature of the system. Since the energizing signal is a pulsed signal, it includes groups of frequencies. The frequency that corresponds to a false lock is influenced by the pulse repetition frequency, the Q of the sensor, and the duty cycle of the RF burst. For example, a constant pulse repetition frequency adds spectral components to the return signal at harmonic intervals around the resonant frequency of the sensor, which can cause a false lock. In one embodiment, false locks occur at approximately 600 kHz above and below the resonant frequency of the sensor. To determine a false lock, the characteristics of the signal are examined. For example, pulse repetition frequency dithering and/or observing the slope of the baseband signal are two possible ways of determine a false lock. In one embodiment where the system locks on a sideband frequency, the signal characteristics correspond to a heartbeat or a blood pressure waveform.

The second type of false lock arises due to a reflection or resonance of another object in the vicinity of the system. This type of false lock can be difficult to discern because it generally does not correspond to a heartbeat or blood pressure waveform. The lack of frequency modulation can be used to discriminate against this type of false lock. Changing the orientation of the magnetic loop also affects this type of false lock because the reflected false lock is sensitive to the angle of incidence.

The third type of false lock arises due to switching transients caused by switching the PIN diodes and analog switches in the RF path. These transients cause damped resonances in the filters in the receive chain, which can appear similar to the sensor signal. Typically, these types of false locks do not correspond to a heartbeat or blood pressure waveform because they are constant frequency. These types of false locks are also insensitive to orientation of the magnetic loop.

To avoid the first type of false lock, the present invention determines the slope of the baseband signal (the phase difference signal at point 330). In, one embodiment, if the slope is positive, then the lock is deemed a true lock. However, if the slope is negative, then the lock is deemed a false lock. In another embodiment, a negative slope is deemed a true lock and a positive slope is deemed a false lock. The slope is determined by looking at points before and after the phase difference signal goes to zero. The slope can be determined in a number of different ways, including but not limited to, using an analog differentiator or multiple sampling. FIGS. 4(a) and 4(b) illustrate a true lock and a false lock respectively, when a positive slope indicates a true lock. In one embodiment, if a false lock is detected, then the signal strength is suppressed so that the signal strength appears to the processor 322 to be below the threshold and the system continues to search for the center frequency. In other embodiments, any non-zero slope can be interpreted as a false lock resulting in zero signal strength.

Figure 5:
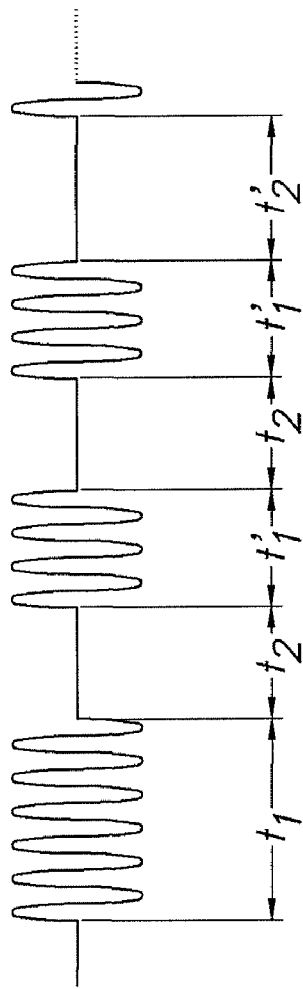
FIG. 5 illustrates frequency dithering, in accordance with an embodiment of the invention.

The system can also use frequency dithering to avoid the first type of false lock. Since the spectral components associated with a constant pulse repetition frequency can cause a false lock, dithering the pulse repetition frequency helps avoid a false lock. By dithering the pulse repetition frequency, the spectral energy at the potential false lock frequencies is reduced over the averaged sampling interval. As shown in FIG. 5, the energizing signal includes an on time t1 and an off time t2. The system can vary the on time or the off time to vary the PRF (PRF 1/(t1+t2)). FIG. 5 illustrates different on times (t1, t1') and different off times (t2, t2'). By varying the PRF, the sidebands move back and forth and the average of the sidebands is reduced. Thus, the system locks on the center frequency rather than the sidebands. The PRF can be varied between predetermined sequences of PRFs or can be varied randomly.

Reducing Switching Transients

Figure 6:
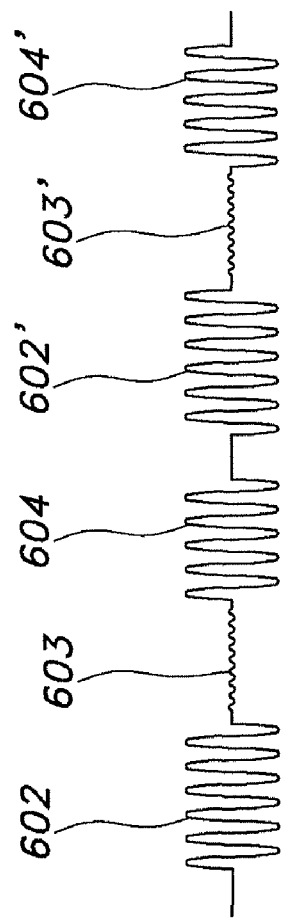
FIG. 6 illustrates phase dithering in accordance with an embodiment of the invention.

The coupling loop switches between an energizing, mode and a coupling mode. This switching creates transient signals, which can cause the third type of false lock. Phase dithering is one method used to reduce the switching transients. As shown in FIG. 6, the system receives a switching transient 603 between the end of the energizing signal 602 and the beginning of the coupled signal 604. To minimize the transient, the phase of the energizing signal may be randomly changed. However, changing the phase of the energizing signal requires that the system redefine zero phase for the system. To redefine zero phase for the system, the phase of DDS2 is changed to match the change in phase of the energizing signal. Thus, the phase of the energizing signal 602' and the coupled signal 604' are changed, but the phase of the transient signal 603' is not. As the system changes phase, the average of the transient signal is reduced.

Changing the resonant frequency of the antenna as it is switched from energizing mode to coupling mode also helps to eliminate the switching transients. Eliminating the switching transients is especially important in the present invention because of the characteristics of the coupled signal. The coupled signal appears very quickly after the on period of the energizing signal and dissipates very quickly. In one embodiment, the invention operates in a low power environment with a passive sensor so that the magnitude of the coupled signal is small. However, the invention is not limited to working with a passive sensor.

The coupling loop is tuned to a resonant frequency that is based upon the sensor parameters. Changing the capacitors or capacitor network that is connected to the coupling loop changes the resonant frequency of the antenna. The resonant frequency typically is changed from approximately $1/10$% to 2% between energizing mode and coupled mode. In some embodiments, the coupling loop is untuned.

Additional alternative embodiments will be apparent to those skilled, in the art to which the present invention pertains without departing; from its spirit and scope. For example, the system can operate with different types of sensors, such as non-linear sensors that transmit information at frequencies other than the transmit frequency or sensors that use backscatter modulations. Accordingly, the scope of the present invention is described by the appended claims and is supported by the foregoing description.

What is claimed is:

1. A method for determining a resonant frequency of a wireless sensor, comprising:
   providing a calibration cycle, wherein the calibration cycle includes:
   generating an energizing signal, by a base unit;

receiving a calibration signal, by the base unit via a coupling loop; and comparing the energizing signal and the calibration signal to determine a phase difference; and providing a measurement cycle, wherein the measurement cycle includes:

energizing the wireless sensor, by the base unit;

receiving a sensor signal from the wireless sensor, by the base unit via the coupling loop;

determining a characteristic of the sensor signal; and using the characteristic to determine the resonant frequency of the wireless sensor.

2. The method of claim 1, wherein the characteristic is amplitude and wherein using the characteristic to determine the resonant frequency of the wireless sensor comprises determining that a frequency of the sensor signal at a maximum amplitude of the sensor signal corresponds to the resonant frequency of the sensor.

3. The method of claim 1, wherein the characteristic is sensor group delay and wherein using the characteristic to determine the resonant frequency of the wireless sensor comprises determining that a frequency of the sensor signal at a maximum sensor group delay of the sensor signal corresponds to the resonant frequency of the sensor.

4. The method of claim 1, wherein the calibration signal corresponds to an energizing leakage signal.

5. The method of claim 1, further comprising:
adjusting a phase of the energizing signal; and
providing additional calibration cycles until the phase difference between the energizing signal and the calibration signal corresponds to a predetermined value.

6. The method of claim 1, further comprising:
adjusting a frequency of the energizing signal; and
providing another measurement cycle.

7. A system for determining a resonant frequency of a wireless sensor, comprising:
a transmitter in a base unit operable to transmit an energizing signal during a calibration cycle and during a measurement cycle;
a receiver in the base unit operable to receive a calibration signal during the calibration cycle and a sensor signal from the wireless sensor during the measurement cycle via a coupling loop,
a plurality of signal processing components; and
at least one processor;
wherein the signal processing components and the at least one processor are operable to:
compare the energizing signal and the calibration signal to determine a phase difference during the calibration cycle,
determine a characteristic of the sensor signal during the measurement cycle, and
use the characteristic of the sensor signal to determine the resonant frequency of the wireless sensor.

8. The system of claim 7, wherein the characteristic is amplitude and the signal processing components and the at least one processor are operable to determine a maximum amplitude of the sensor signal and use a frequency of the sensor signal at the maximum amplitude of the sensor signal to determine the resonant frequency of the sensor.

9. The system of claim 7, wherein the characteristic is sensor group delay and the signal processing components and the at least one processor are operable to determine a maximum sensor group delay and use a frequency of the sensor signal at the maximum sensor group delay to determine the resonant frequency of the sensor.

10. The system of claim 7, wherein the signal processing components include a first phase lock loop (PLL) and the first PLL is operable to adjust a phase of the energizing signal.

11. The system of claim 10, wherein the signal processing components include a second phase lock loop (PLL) and the second PLL is operable to adjust a frequency of the energizing signal.

12. A method for determining a resonant frequency of a wireless sensor, comprising:
energizing, by a base unit, the wireless sensor using an energizing signal, wherein a phase difference between the energizing signal and an energizing leakage signal received by a coupling loop is a predetermined value;
receiving a sensor signal from the wireless sensor by the base unit via the coupling loop;
determining a characteristic of the sensor signal; and
using the characteristic of the sensor signal to determine the resonant frequency of the wireless sensor.

13. The method of claim 12, wherein energizing the wireless sensor using an energizing signal, comprises:
generating the energizing signal by the base unit;
receiving the energizing leakage signal by the base unit;
comparing the energizing signal and the energizing leakage signal to determine the phase difference; and
adjusting the phase of the energizing signal until the phase difference is the predetermined value.

14. The method of claim 12, wherein the characteristic is amplitude and wherein using the characteristic to determine the resonant frequency of the wireless sensor comprises determining that a frequency of the sensor signal at a maximum amplitude of the sensor signal corresponds to the resonant frequency of the sensor.

15. The method of claim 12, wherein the characteristic is sensor group delay and wherein using the characteristic to determine the resonant frequency of the wireless sensor comprises determining that a frequency of the sensor signal at a maximum sensor group delay of the sensor signal corresponds to the resonant frequency of the sensor.

16. The method of claim 12, further comprising:
adjusting a frequency of the energizing signal until a phase difference between the energizing signal and the sensor signal corresponds to a predetermined value.

* * * * *